US006387669B1

(12) United States Patent
Truex et al.

(10) Patent No.: US 6,387,669 B1
(45) Date of Patent: May 14, 2002

(54) METHODS FOR PRODUCING HYDROGEN (BI) SULFIDE AND/OR REMOVING METALS

(75) Inventors: Michael J. Truex, Richland; Brent M. Peyton, Pullman; James J. Toth, Kennewick, all of WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/478,264

(22) Filed: Jan. 5, 2000

Related U.S. Application Data

(63) Continuation-in-part of application No. 09/217,767, filed on Dec. 21, 1998, now abandoned.

(51) Int. Cl.⁷ .............................. C12P 3/00; C12S 1/02; C02F 3/00
(52) U.S. Cl. ...................... 435/168; 435/262; 210/601; 210/610; 210/611
(58) Field of Search .................................. 435/262, 168; 210/601, 610, 611

(56) References Cited

U.S. PATENT DOCUMENTS

| | | | |
|---|---|---|---|
| 4,200,523 A | | 4/1980 | Balmat ........................... 210/4 |
| 4,354,937 A | * | 10/1982 | Hallberg ...................... 210/607 |
| 4,614,588 A | * | 9/1986 | Li ............................... 210/603 |
| 4,735,723 A | | 4/1988 | Mulder ........................ 210/603 |
| 5,196,176 A | | 3/1993 | Buisman .................. 423/242.2 |
| 5,338,460 A | | 8/1994 | Yen ............................. 210/724 |
| 5,554,290 A | | 9/1996 | Suthersan .................... 210/610 |
| 5,587,079 A | | 12/1996 | Rowley et al. ............. 210/603 |

OTHER PUBLICATIONS

Barnes et al. Simultaneous microbial removal of sulfate and heavy metals from waste water. Trans. Inst. Min. Metall., Sect. C (1992), 101 (Sep.–Dec.), C183–C189.*
A.L. de Vegt, H. Dijkman, C.L. Buisman, "Hydrogen Sulfide Produced From Sulfate By Biological Reduction for Use in Metallurgical Operations." Mar. 9, 1998, pp. 1–5.
Paques, "Heavy Metals Removal.", pp. 1–2, 1998.
Friedrich Widdel, "Microbiology and Ecology of Sulfate– And Sulfur–Reducing Bacteria", pp. 469–585. 1987.

* cited by examiner

*Primary Examiner*—Irene Marx
*Assistant Examiner*—Vera Afremova
(74) *Attorney, Agent, or Firm*—Stephen R. May; Douglas E. McKinley, Jr.

(57) ABSTRACT

The present invention is a process wherein sulfide production by bacteria is efficiently turned on and off, using pH adjustment. The adjustment of pH impacts sulfide production by bacteria by altering the relative amounts of $H_2S$ and $HS^-$ in solution and thereby control the inhibition of the bacterial metabolism that produces sulfide. This process can be used to make a bioreactor produce sulfide "on-demand" so that the production of sulfide can be matched to its use as a metal precipitation reagent. The present invention is of significance because it enables the use of a biological reactor, a cost effective sulfide production system, by making the biological reactor produce hydrogen sulfide "on demand", and therefore responsive to production schedules, waste stream generation rate, and health and safety requirements/goals.

16 Claims, 3 Drawing Sheets

METHODS FOR PRODUCING HYDROGEN (BI) SULFIDE AND/OR REMOVING METALS

This application is a Continuation-in Part of application Ser. No. 09/217,767 filed Dec. 21, 1998 now abandoned.

This invention was made with Government support under Contract DE-AC0676RLO1830 awarded by the U.S. Department of Energy. The Government has certain rights in the invention.

FIELD OF THE INVENTION

The present invention relates to producing hydrogen (bi)sulfide with microorganisms. The hydrogen (bi)sulfide may be used for removal of metals from a waste stream.

As used herein, the term "hydrogen (bi)sulfide" is defined as hydrogen sulfide and/or hydrogen bisulfide.

BACKGROUND OF THE INVENTION

Industrial (e.g. metal finishing and electronics industries) metal-laden waste streams and environmental restoration activities (e.g., mine drainage) are the focus for treatment. Treatment of these waste streams represents a significant economic cost. The current baseline treatment is conventional pH neutralization followed by precipitation of the metal as sludge, such as by the addition of lime or sodium hydroxide to neutralize the waste and precipitate the metal (s). The conventional process produces large volume of difficult-to-handle, hydroxide sludge that must be disposed of or blended with other material to make it suitable for smelting (reuse). Other technologies can be applied to remove metals from waste streams and produce more manageable sludges/secondary wastes, but these technologies are typically more expensive than the conventional process due to higher energy consumption or higher reagent cost. (e.g., reverse osmosis, ion exchange, chemical sulfide precipitation). For example, U.S. Pat. No. 5,338,460 describes removing dissolved heavy metals from an aqueous stream by reacting at least one of the metals with a water-soluble inorganic sulfide at a controlled pH between about 2 and 3.5 within a temperature range of between 100 degrees F. and 212 degrees F. However, this process has not been commercially accepted because chemical sources of sulfides for use in precipitation processes (e.g., sodium sulfide) are expensive such that chemical sulfide precipitation costs are typically higher than costs for baseline technologies.

The use of sulfate-reducing bacteria (SRB) has been proposed as a cost effective means to remove metals from waste streams. In fact, there are several successful applications of this process in operation for environmental restoration efforts (mine drainage treatment and groundwater treatment) de Vegt, A. L., H. Dijkman, and C. J. Buisman. 1998. "Hydrogen Sulfide Produced from Sulfate by Biological Reduction for use in Metallurgical Operations." In: Proceedings of the Society for Mining, Metallurgy, and Exploration Annual Meeting, Orlando Fla., Mar. 9–11, 1998. SRB can be used to remove metals for waste streams because these bacteria produce sulfides (hydrogen sulfide ($H_2S$) and bisulfide (HS—)), that react with metals to form insoluble metal precipitates. Thus, systems can be designed that induce sulfide generation by the SRB and then contact the resulting sulfide with metal-laden waste streams such that the metals precipitate from solution and are removed from the waste stream.

SRB can be found in nature in a number of environments in which some portion is anaerobic (e.g., municipal sewage sludge, river and marine sediments, aquifers). SRB typically live in conjunction with other bacteria that convert complex organic molecules into the more simple organic molecules and hydrogen that SRB can metabolize. SRB link oxidation of an organic or hydrogen to reduction of sulfate (and in some cases other oxidized sulfur compounds) to produce sulfides as a product. During metabolism, some SRB can completely oxidize small organic acids to CO2 and water. Other SRB incompletely oxidize organic acids such as lactate to acetate. SRB can survive some exposure to oxygen, but are strict anaerobes and only reduce sulfate in the absence of oxygen. Sulfate is the primary electron acceptor for SRB, although, some species/strains can reduce other compounds (Widdel, F. 1988. "Microbiology and Ecology of Sulfate- and Sulfur-Reducing Bactieria." In: A. J. B Zehnder (Ed.). *Biology of Anaerobic Microorganisms*. Wiley Interscience, New York).

As is taught by U.S. Pat. No. 5,587,079, sulfides produced by SRB may be used for metal sulfide precipitation. The reaction chemistry of the precipitation process is:

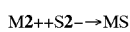

where M2+ represents a metal ion having a valence of 2+, S2− represents a sulfide ion with a valence of 2−, and MS represents a metal sulfide compound (solid precipitate).

Bacteria are used to provide hydrogen sulfide and carbonate compounds for treating solutions containing metal ions. By controlling the addition of hydrogen sulfide and carbonate compounds to the solution, the preferential isolation of particular metal sulfide concentrates may be accomplished in separate precipitation steps, each with a specific pH and sulfide dosage.

U.S. Pat. No. 5,554,290 reports use of microbially-generated (biogenic) sulfide for metals precipitation for in situ environmental restoration. In this method, nutrients that stimulate indigenous bacteria to produce sulfide are injected into the subsurface aquifer. The sulfide precipitates metals present and the precipitate remains in situ.

In U.S. Pat. No. 4,735,723, waste water containing sulfate and organic material is purified by anaerobic biological waste water treatment where at least 80% of the sulfate is converted into hydrogen sulfide in an acidification process and at least 70% of the resulting hydrogen sulfide is removed from the waste stream.

However, although the use of SRBs produce sulfides useful in the removal of heavy metals from process streams, such processes currently known in the art are essentially steady-state processes that have not heretofore been used for "on-demand" production of sulfides for metal removal. Such limitations are a result of the fact that the sulfide production rate of a biological reactor is proportional to the concentration of viable bacteria in the reactor. That is, the overall production rate is the production rate of a single bacterium (or a specific production rate per gram of bacteria) multiplied times the number of bacteria (or total grams) in the reactor. The concentration of bacteria in the reactor is hereinafter termed the biomass concentration. A material balance for biomass concentration in a reactor is as follows.

Mass rate of change in biomass=rate of change due to growth−rate of change due to decay−rate of change due to outflow.

The rate of change due to growth represents the bacterial growth from metabolism of a substrate, i.e., substrate conversion. The rate of change due to decay is the decrease in biomass concentration due to maintenance energy requirements and endogenous metabolism which is commonly related to the use of cellular materials or extra-cellular materials as a substrate. In a reactor at steady-state operation, the bacterial growth is balanced by the loss of bacteria in the reactor effluent and the rate of bacterial decay. At this steady state condition, the sulfide production rate of the reactor is stable.

For reliable "on-demand" sulfide production, a reactor must be shut down and then restarted at the same conversion rate (i.e., at the same steady state condition). Therefore, the biomass concentration must be maintained at the same concentration during the time intervals between active demand for sulfide. However, currently, when the inflow and outflow to the reactor are stopped and substrate is not added to the reactor, over time, the biomass decay rate will predominate such that the biomass concentration decreases. To restart the reactor thus requires either adding a charge of new bacteria to return the reactor to the previous level of biomass concentration, or allowing sufficient time for the remaining bacteria to multiply to the previous level of biomass concentration.

Hence, for reliable "on-demand" sulfide production, there remains a need for a method to control the process of microbial production of sulfides wherein the rate of sulfide production may be first halted, and then resumed, without the necessity of adding additional bacteria or waiting for the remaining bacteria to multiply and increase the biomass concentration to the prior level. The need additionally extends to match sulfide production with demand, for example metal precipitation.

SUMMARY OF THE INVENTION

The present invention provides a robust and stable means to stop and start sulfide ($H_2S$) production in a biological system, without diminishing the longterm performance of the biological system, such that the biological system operates as if it were a container of $H_2S$ gas with a control valve.

Advantages of the present invention include 1) coupling microbial production to the use of $H_2S$ [ $H_2S$ is toxic and thus preferably not produced in excess of demand], 2) stopping the production of sulfide when it is not needed for metal precipitation, thereby conserving consumables, reducing costs, and increasing safety, 3) stopping and then re-starting the sulfide production without impacting the efficiency of the production mechanism (bioreactor).

The critical feature of the present invention is the careful control and rapid changes of pH within a bioreactor affecting a rapid change in the distribution of H2S and HS—, which has rapid effects on SRB metabolism. SRB are inhibited by $H_2S$, and not by HS—, and the relative concentration of H2S and HS— in solution is determined by and very sensitive to the solution pH. The relevant $H_2S$ inhibition kinetics are presented in Reis et al., (1992). The pKa of $H_2S$ (pH at which the concentrations of $H_2S$ and HS— are equal) is about 7. Thus, in general, at pH somewhat lower than pH 7, more $H_2S$ is present in solution than HS—. At pH somewhat higher than pH 7, more HS— is present in solution than $H_2S$. While other known factors such as pH dependence of SRB activity and other inhibitors (e.g, undissociated acetate) can impact SRB metabolism, within a bioreactor where the concentration of sulfides are high, $H_2S$ inhibition can be used as the primary mechanism affecting sulfide production rate. Thus, by adjusting and controlling the pH within a pH range that does not damage the bacteria, the sulfide production rate can be quickly adjusted from between essentially zero and the maximum rate.

Increasing the inhibition of SRB acts to simultaneously slow the activity of the bacteria to essentially a standstill, thereby halting the production of sulfides, while simultaneously substantially slowing or eliminating bacterial decay and the subsequent loss of biomass concentration. By preserving biomass concentration with pH modification, when necessary, the reactor may be made to resume the production of sulfides at essentially the same rate, by returning the pH of the reactor to its prior level. Since the pH of the bioreactor may be rapidly changed through the introduction of acids and bases, the method of the present invention allows the production of sulfides in a bioreactor to be turned off and on to meet demand with no sacrifice in the rate of sulfide production. As used herein, when the pH of a bioreactor is adjusted such that the activity of the bacteria and bacterial decay are simultaneously substantially slowed or stopped, the SRBs are said to be in a state of suspended animation. It is preferred that the activity of the bacteria and bacterial decay be completely stopped, however, as will be appreciated by those having skill in the art, while the introduction of acids and bases into the bioreactor will rapidly change the pH of the bioreactor, and thereby achieve the desired state of suspended animation, slight activity of the bacteria and/or bacterial decay may persist. Thus, the present invention should be understood to encompass situations wherein some slight activity and/or decay persists. Thus, as used herein, when the rate of reduction of an oxidized sulfur compound is said to be reduced from a predetermined rate to substantially zero, the applicant intends that "substantially zero" be defined as preferably less than or equal to 10%, more preferably less than or equal to 5% and most preferably less than or equal to 1% of the predetermined rate of reduction. Also, as used herein, when a rate of decay of bacteria is said to be substantially zero, the applicant intends that "substantially zero" be defined as a rate of decay wherein preferably less than 2%, more preferably less than 0.5%, and most preferably less than 0.1% of the biomass concentration is lost in a twenty-four hour period. Finally, as used herein, when a rate of reduction of said oxidized sulfur compound is said to be substantially returned to the predetermined rate, the applicant intends that "substantially returned" be defined as preferably at least 90%, more preferably at least 95%, and most preferably at least 99% of the predetermined rate.

In a preferred embodiment, the rate of sulfide production is relative to the demand for sulfide to precipitate at least one metal from a metal-containing process waste stream. In the preferred embodiment of the invention, a first waste stream contains a quantity of metal ions requiring removal and disposal. A second process stream contains a quantity of sulfates, and can be supplemented with an organic compound to enhance growth of SRBs. The second process stream is introduced into a bioreactor and the pH is controlled from about 5.0 to about 9.0. The bioreactor can be operated in one of two distinct states: 1) at a relatively low pH, such that the SRBs are maintained in a state of suspended animation; and 2) at a relatively higher pH wherein the SRBs are actively producing sulfide for use in precipitation of metals in the first process stream.

The process of the present invention is of significant economic import to generators of metal-laden waste streams because it enables the use of a cost effective sulfide production system, biological reactors, by making the biological reactors produce sulfide "on demand", and therefore responsive to production schedules, waste stream generation rate, and health and safety requirements/goals. Bioreactors use non-hazardous consumables to produce the hazardous metal precipitation reagent $H_2S$. With on-site, on-demand production of this hazardous, but effective reagent, industries can avoid storage of large quantities of hazardous material (i.e., avoid storing and using $H_2S$ gas) and tune the production of a hazardous reagent to cyclical use patterns (e.g., daily production shifts).

$H_2S$ is a preferred metal precipitation reagent because it can remove metals from aqueous streams down to residual concentrations lower than many other precipitation technologies (e.g., lime precipitation) and it does not add total dissolved solids to the waste stream. Because it only adds protons to the aqueous stream while removing the metals, use of $H_2S$ allows the possibility of water recycle/reuse within a facility.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWINGS

FIG. 1a is a schematic representation of the process of an embodiment of the present invention.

FIG. 1b is a schematic representation of the process of an embodiment of the present invention wherein a sulfide laden stream is mixed with a metal laden stream.

DESCRIPTION OF THE PREFERRED EMBODIMENT(S)

Figure 1C:
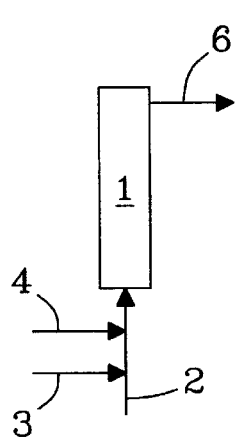
FIG. 1c is a schematic representation of the process of an embodiment of the present invention wherein the sulfide stream is gaseous.
Figure 1C:
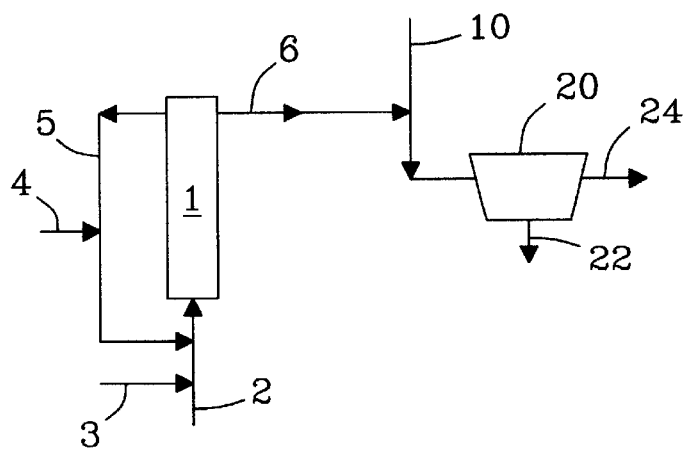
Figure 1C:
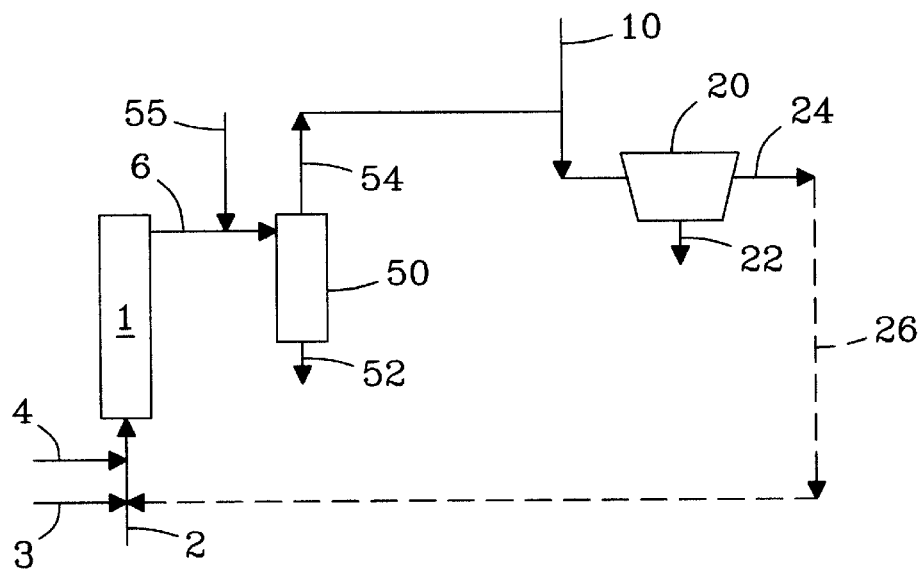

As illustrated schematically in FIG. 1a, the process of the present invention is method of stopping and starting sulfide production from a bioreactor 1 containing at least one species of a bacteria capable of reducing an oxidized sulfur compound to a sulfide compound in an aqueous media wherein an oxidized sulfur compound 2 is introduced into the bioreactor 1, together with a feed or substrate (e.g. ethanol) 3. While the bioreactor is in operation, the sulfide produced is removed as part of an aqueous effluent 6. The combination of continuously introducing the oxidized sulfur 2 and feed 3, together with the continuous removal of sulfide 6 and maintaining the aqueous media at an appropriate pH, allows the bacteria to reduce oxidized sulfur introduced into the bioreactor 1 at a predetermined, steady state rate. The oxidized sulfur compound 3 includes but is not limited to $SO_4^{(2-)}$, $SO_3^{(2-)}$, $S_2O_3^{(2-)}$, and combinations thereof. The method of the present invention thus has the steps of: stopping the reduction of the oxidized sulfur compound in the bioreactor by rapidly decreasing the pH of the aqueous media to a level at which H2S is the dominant sulfide species in the bioreactor. H2S inhibition of SRB then lowers the rate of reduction of said oxidized sulfur compound to substantially zero and the rate of decay of said bacteria to substantially zero. Restarting sulfide production is accomplished by raising the pH of the aqueous media to a level at which HS— is the predominant sulfide species. Since HS— is non-inhibitory to SRB, the rate of reduction of said oxidized sulfur compound is substantially returned to the predetermined rate. The pH may be adjusted by adding a compound 4 to the bioreactor. To stop and start production of sulfide compounds in the bioreactor, pH ranges from about 5.0 to about 9.0 should be used. Where a recycle 5 (FIG. 1b) is used, the compound 4 may be added to the recycle 5.

The reactor pH required to achieve a specific amount of $H_2S$ inhibition, and thereby set a rate of sulfide production, is dependent on the total concentration of sulfide in the reactor and other reactor specific parameters including but not limited to the biofilm thickness, the concentration of other chemical species such as acetate, the specific microbial population, and combinations thereof.

Figure 2:
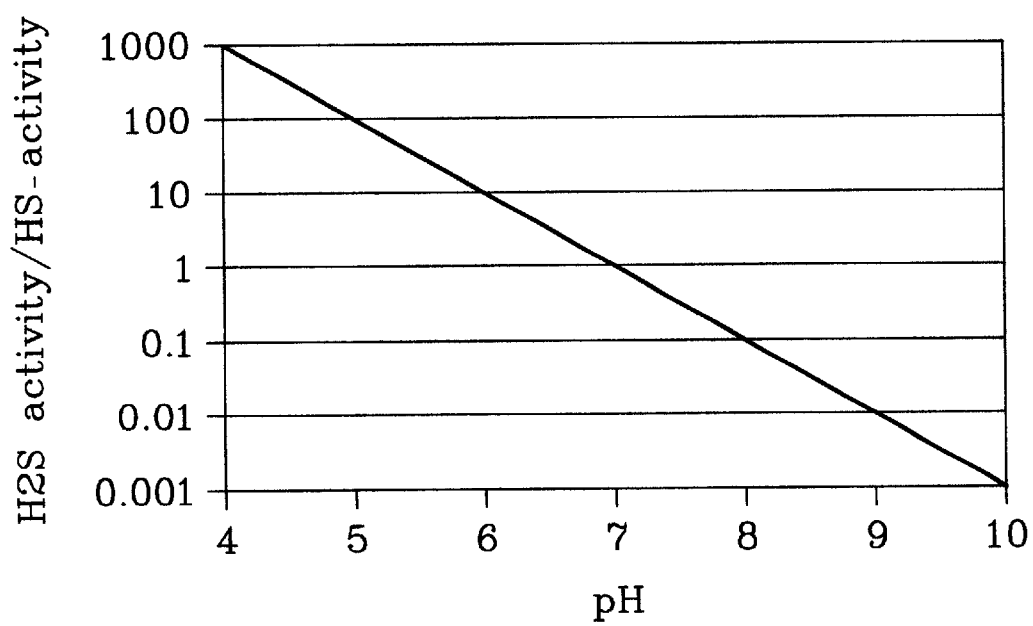
FIG. 2 is a graph of activity versus pH.

Ignoring other reactor specific parameters, two examples illustrate the relationship between total sulfide concentration and the pH required for the desired inhibition of sulfide production. These two simplified examples demonstrate that selecting the correct reactor pH is dependent on the total sulfide concentration in the reactor. For both examples, it is assumed that, for the given reactor, a concentration of 15 mM of $H_2S$ is needed to achieve the desired inhibition of the sulfide production rate. It is further assumed that the activity of each species equals its concentration for the calculations. In the first example, the total sulfide concentration (taken as the sum of $H_2S$ and HS— only for this example) is 30 mM. FIG. 2 shows the relationship, based upon equilibrium chemistry, of the ratio of $H_2S$ activity with pH. To achieve an $H_2S$ concentration of 15 mM in a reactor containing 30 mM of total sulfide, the pH must be adjusted such that the ratio $H_2S$/HS— concentrations equal one (15 mM $H_2S$ and 15 mM HS—). To achieve an H2S/HS— ratio of one, a pH of 7 is required. In the second example, the total sulfide concentration ($H_2S$ and HS—) is 20 mM (10 mM less than in the first example). In this example, to achieve an $H_2S$ concentration of 15 mM, the $H_2S$/HS— ratio must be three. To achieve an $H_2S$/HS—ratio of three, a pH of about 6.5 is required. These examples illustrate the relationship between pH and total sulfide concentration. It will be understood by those of skill in the art that consideration of other reactor specific parameters may change the pH required for producing a state of suspended animation.

The sulfide containing effluent 6 may be used directly in a metal laden waste stream 10 to precipitate the metal. A precipitate removal vessel or precipitate separator 20 may be used to remove the precipitate 22 and form a metal-free stream 24. However, the metal-free stream 24 may need further processing to remove other compounds. As will be recognized by those having skill in the art, the metal-free stream 24 may then directed through a plurality of chemical processes (not shown) in a treatment scheme. Alternatively, as shown in FIG. 1c, the sulfide containing effluent 6 may be passed to a stripper 50 providing an aqueous waste stream 52 and a sulfide gas stream 54. An additional acid stream 55 added to the sulfide containing effluent 6 is beneficial when a sulfide gas stream 54 is generated. The sulfide gas stream 54 is then combined with a metal laden waste stream 10 to precipitate the metal as in FIG. 1b. However, in this case, the metal-free stream 24 is sufficiently clean as to be useful for re-use, recycle or as a feed stream 26 to the bioreactor 1. It may be desirable or necessary to adjust the pH of the feed stream 26 before putting it into the bioreactor 1.

In a preferred embodiment (FIG. 1d) an oxidized sulfur compound-containing process stream 2, is used to produce a sulfide containing stream 6 that is used to precipitate metal from the waste process stream 10. The metal-containing stream 10 may be a process stream including but not limited to mining process, printed circuit board manufacture, electroplating, and combinations thereof. The process of the present invention may be used whenever a process stream contains at least one metal ion that can be precipitated by a (bi)sulfide, and can include (by way of example only, and not intending to be limiting): Cu. Ag, Hg, Bi, Fe, Cd, Pb, Zn, Co, Ni, Mn, As, Cr and combinations thereof. It is believed that the process of the present invention will be effective in reducing the concentrations of metals in the first process stream from influent concentrations in the 10's of g/L range to effluent concentrations that are near the solubility limit of the specific metal precipitate (typically ug/L to low mg/L range). The metal precipitate may be a metal sulfide, or a reduced metal precipitate for example $CrOH_3$ or combinations thereof.

The stream 10 is directed into a metals contactor 60, which allows for transfer of the $H_2S$ gas 54 into the aqueous stream where it can react with the metal ions.

The second oxidized sulfur compound-containing process stream 2 is directed into the bioreactor 1, which may take any conventional form, such as a fluidized bed, continuously stirred tank reactor or other form of bioreactor. A pH adjusting compound or supply 4 is provided as needed to supply the bioreactor with either a basic or acidic solution into the recycle loop 5. If necessary, organic growth media 3 may be added to the process stream 2 before entering the bioreactor 1. Sulfide produced in the bioreactor 1 is removed through line 6 and directed to an $H_2S$ stripper 50. An aqueous waste stream 52 is removed from stripper 50 and sulfide gas 54 is provided to the metals contactor 60. Recycle of carrier gas, preferably a gas substantially free of oxygen (e.g. $CO_2$) from the contactor 60 to the stripper 50 is through recycle line 62. Substantially free of oxygen means commercially pure or less than 5 vol % oxygen, preferably less than 3 vol % oxygen and most preferably less than about 1 vol %. The sulfide solution from the bioreactor 1 in the line 6 is preferably at a pH less than the pH of the bioreactor 1 upon entering the stripper 50. Hence, an acid 55 is added to lower the sulfide solution pH to less than the pH of the bioreactor 1. The contactor outlet stream or slurry 64 containing metal precipitate is directed into, for example, a settling tank 20, where the metal precipitate 22 and a metals-free aqueous stream 24 are removed. All or a portion of stream 24 may be recycled 26 to the bioreactor 1 or may be reused or recycled for other purposes.

The bacteria utilized in the bioreactor 1 can be any bacteria which, under anaerobic conditions, utilize oxidized sulfur compound(s) as an electron acceptor in their metabolism and produce sulfide compounds. The main genera of bacteria capable of sulfate reduction are Desulfovibrio and Desulfotomaculum. There are currently in excess of 15 species identified in these two genera. Other bacteria are members of the genera Desulfococcus, Desulfomonas, Desulfonema and Desulfurococcus. These bacteria may be isolated from environmental sources or purchased from commercial vendors.

Figure 1D:
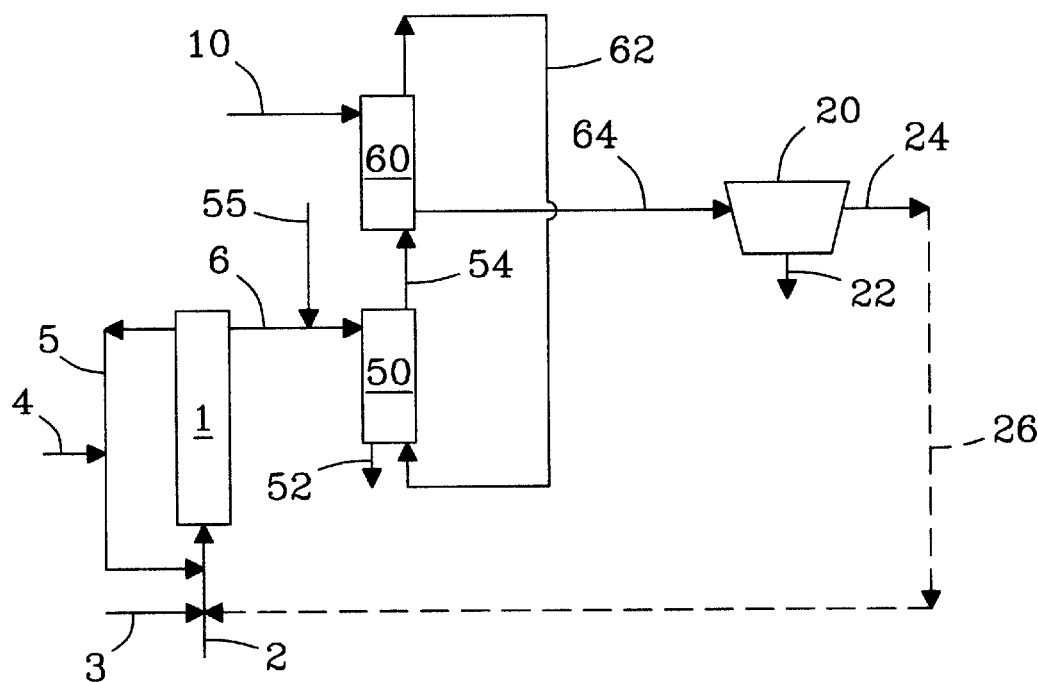
FIG. 1d is a schematic representation of the process of the preferred embodiment of the present invention using a gaseous sulfide to a metals contactor.

The apparatus of FIG. 1d permits rapid changes in pH within the bioreactor 1 as a means to control the inhibitory effects of $H_2S$ on SRB to rapidly affect the sulfide production rate across a range between zero and the maximum steady state production rate. By rapidly distributing acid or base 4 to the bioreactor 1, through $H_2S$ inhibition, the metabolism of the SRBs is rapidly altered, and thereby the production rate of sulfide is affected. Addition of acid lowers the pH and therefore shifts the ratio of $H_2S/HS$— toward higher $H_2S$ concentrations, thus reducing or stopping SRB activity through $H_2S$ inhibition. If sulfide production is halted, the SRBs can be maintained in the bioreactor in a state of suspended animation until further production of sulfide is required. Re-initiation of sulfide production, through the addition of a base that shifts the $H_2S/HS$— ratio toward HS—, is rapid and sulfide production resumes at preferably the same rate as prior to inhibition.

The adjustment of pH should be controlled such that it does not exceed the range of from about pH 5.0 to about 9.0, since SRBs survive without cellular damage within that range. The acids or bases 4 added to the bioreactor 1 can be any conventional solution designed to adjust the solution pH to the desired level. For example, bases such as sodium, potassium, or calcium hydroxides and acids such as sulfuric acid, hydrochloric acid, nitric acid and combinations thereof may be utilized. Organic acids and bases may also be used. However, the stronger inorganic acids and bases are preferred.

EXAMPLE 1

A high recycle, fluidized bed bioreactor 1 was constructed. Granular activated carbon particles were added as the support material. The nominal residence time of the reactor was approximately 20 hours with a 1.1 mL/min influent flow rate. The recycle flow rate was 0.5–1.0 gpm. Conventional mineral salts medium was circulated therethrough, with the influent pH adjusted to 7.0 with NaOH. In addition, an ethanol/yeast extract feed was prepared and added to the reactor as a separate feed stream. A mixed culture of SRBs and other anaerobic bacteria taken from a previously operated bioreactor were used in the bioreactor.

The effluent pH of the material in line 6 was about 7.8. 99% of the sulfide was in the HS—form. Acid 55 was added to the effluent 6 adjusting the effluent pH to 5.9 to convert the HS— to $H_2S$ in the $H_2S$ stripper 50, so that it could be easily sparged and transferred to a trap containing sodium hydroxide (not shown). In the experimental system, the sodium hydroxide trap was used in place of the metal precipitation unit or metal contactor 60 that would be used for an actual application of the system.

Figure 3:
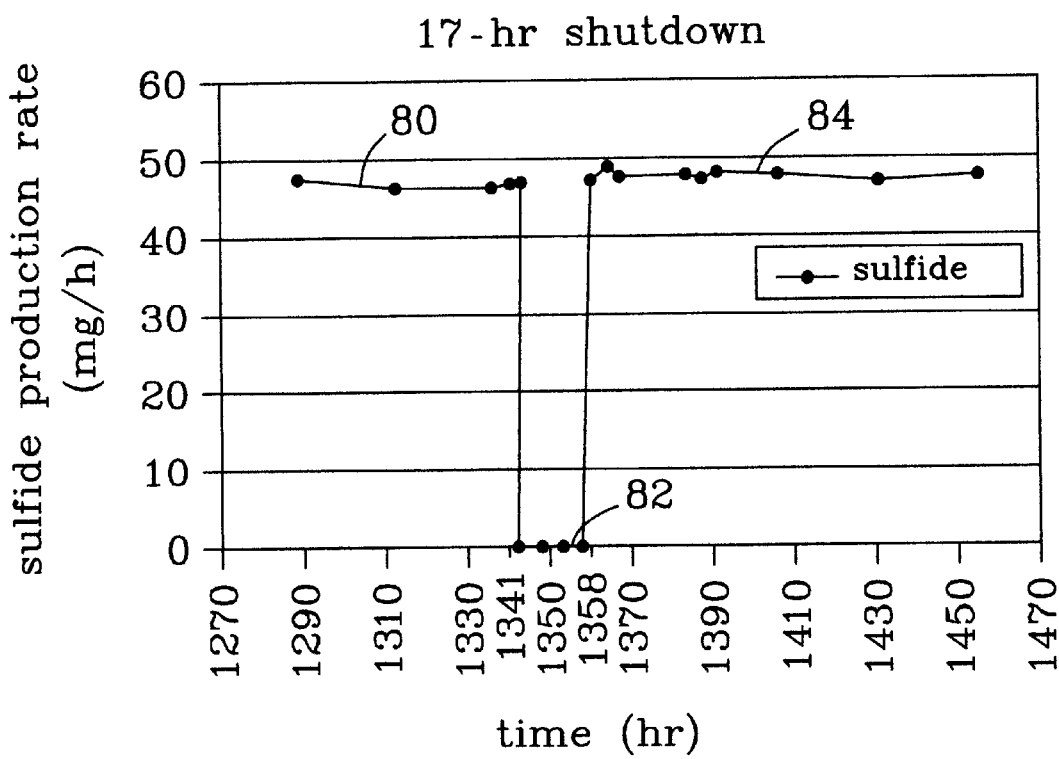
FIG. 3 is a graphic representation of the process of the present invention illustrating sulfide production after a 17 hour shutdown.

FIG. 3, a baseline sulfide production rate 80 of approximately 48 mg/h over a time period of about 1340 hours, hydrochloric acid 4 was added to the bioreactor 1, lowering the pH to 6.0. As can be seen in FIG. 2, sulfide production dropped almost immediately to zero 82, and it was maintained in the "suspended animation" state for approximately 17 hours, at which time sodium hydroxide was added to the bioreactor 1 in order to increase the pH to about 7.5. Sulfide production resumed almost immediately to the same rate 84 as was experienced prior to suspension.

Figure 4:
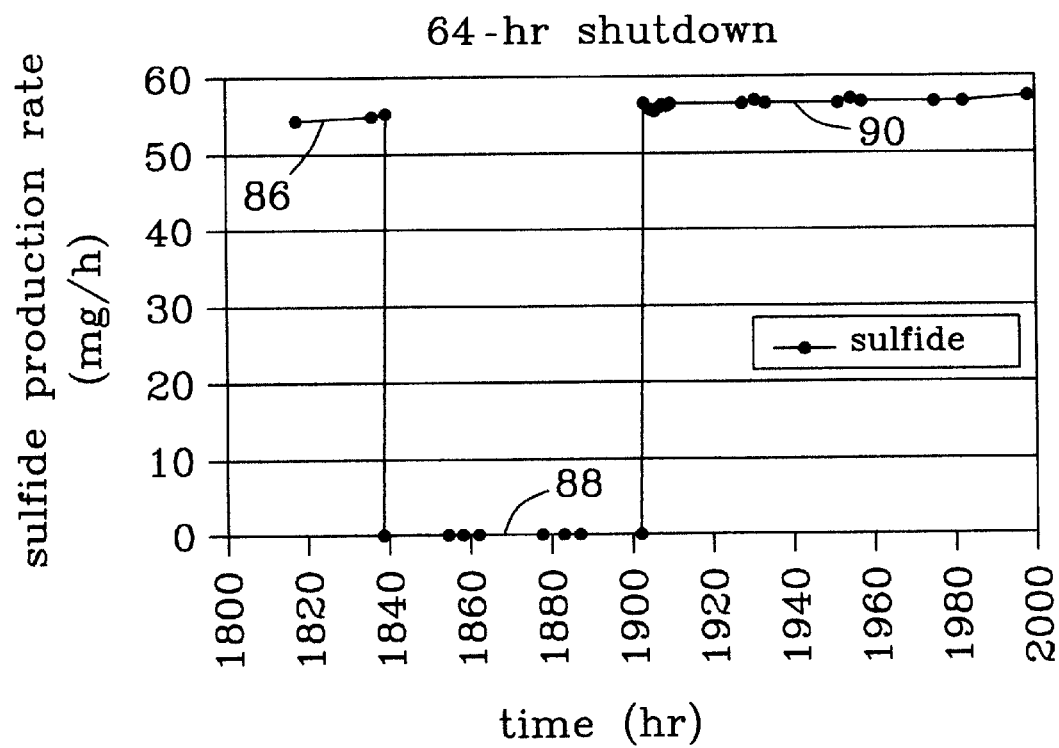
FIG. 4 is a graphic representation of the process of the present invention illustrating sulfide production after a 64 hour shutdown.

As illustrated in FIG. 4, the bioreactor 1 was operated to establish a baseline production 86 of about 55 mg/h of sulfide. The bioreactor 1 was "turned off" 88 as in FIG. 2 by the addition of hydrochloric acid to reduce the pH to 6.0. The bioreactor 1 was maintained in this condition for 64 hours, at which time sodium hydroxide 4 was added to raise the pH to 7.5. The sulfide production was immediately increased 90 to the prior baseline level.

Closure

In summary, the present invention controls production of sulfides to match the demand for metal precipitation and is of benefit to 1) couple the production and use of $H_2S$ which is an effective metal precipitation agent, but is also toxic and thus preferably not produced in excess of demand, 2) stop the production of sulfides when they are not needed to conserve consumables, reduce costs, and increase safety, and 3) allow sulfide production to be turned on and off without impacting the efficiency of the production mechanism (bioreactor). Bioreactors may be adjusted to change or stop the sulfide production rate using techniques other than described in this invention (e.g., altering the amount of substrate feed to the bioreactor), but these other techniques destabilize the bioreactor such that it is difficult to restart and its performance is difficult to control especially after multiple adjustments of the production rate. The invention described herein provides a fast and robust means to turn off and on the sulfide production in a biological system, without diminishing the performance of the biological system, such that the biological system operates essentially as if it were a container of $H_2S$ gas with a control valve.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method of decreasing and increasing sulfide production within a bioreactor containing at least one species of bacteria which is reducing an oxidized sulfur compound to a sulfide compound in an aqueous media at a predetermined rate, the method comprising the steps of:
   a. decreasing the reduction of the oxidized sulfur compound by reducing the pH of the aqueous media to a level at which the rate of reduction of said oxidized sulfur compound is substantially zero and the rate of decay of said bacteria is substantially zero,
   b. increasing the reduction of the oxidized sulfur compound by raising the pH of the aqueous media to a level at which the rate of reduction of said oxidized sulfur compound is substantially returned to the predetermined rate.

2. A method of decreasing and increasing sulfide production within a bioreactor containing at least one species of bacteria which is reducing an oxidized sulfur compound to a sulfide compound in an aqueous media at a predetermined rate, the method comprising the steps of:
   a. decreasing reduction of the oxidized sulfur compound is accomplished by reducing the pH of the aqueous media to a level at which the rate of reduction of said oxidized sulfur compound is less than or equal to ten percent of the predetermined rate, and the rate of decay of said bacteria allows less than two percent of the biomass concentration of the bacteria to decay in a twenty four hour period and
   b. increasing the reduction of the oxidized sulfur compound is accomplished by raising the pH of the aqueous media to a level at which the rate of reduction of said oxidized sulfur compound is returned at least ninety percent of the predetermined rate.

3. The method of claim 2, wherein the
   a. decreasing reduction of the oxidized sulfur compound is accomplished by reducing the pH of the aqueous media to a level at which the rate of reduction of said oxidized sulfur compound is less than or equal to five percent of the predetermined rate, and the rate of decay of said bacteria allows less than one half of one percent of the biomass concentration of the bacteria to decay in a twenty four hour period; and
   b. increasing the reduction of the oxidized sulfur compound is accomplished by raising the pH of the aqueous media to a level at which the rate of reduction of said oxidized sulfur compound is returned at least ninety five percent of the predetermined rate.

4. The method of claim 2, wherein the
   a. decreasing reduction of the oxidized sulfur compound is accomplished by reducing the pH of the aqueous media to a level at which the rate of reduction of said oxidized sulfur compound is less than or equal to one percent of the predetermined rate, and the rate of decay of said bacteria allows less than one tenth of one percent of the biomass concentration of the bacteria to decay in a twenty four hour period; and
   b. increasing the reduction of the oxidized sulfur compound is accomplished by raising the pH of the aqueous media to a level at which the rate of reduction of said oxidized sulfur compound is returned at least ninety nine percent of the predetermined rate.

5. The method of claim 2, wherein the pH is reduced by the addition of an acid.

6. The method of claim 5, wherein the acid is selected from the group consisting of sulfuric acid, hydrochloric acid, nitric acid and combinations thereof.

7. The method of claim 2, wherein the pH is raised by the addition of a base.

8. The method of claim 7, wherein the base is selected from the group consisting of sodium, potassium, calcium hydroxides and combinations thereof.

9. The method of claim 2, wherein the pH is reduced and raised between a range of from about 5.0 to about 9.0.

10. The method as recited in claim 2, further comprising the step of introducing said sulfide into a stream containing at least one metal and precipitating said at least one metal from said stream as metal precipitate.

11. The method as recited in claim 10, wherein said stream is an industrial process stream.

12. The method as recited in claim 11, wherein said stream is directed through a plurality of chemical processes in a treatment scheme.

13. The method as recited in claim 2, wherein said sulfide compound is in an aqueous effluent to which is added an acid for lowering an effluent pH for passing to a stripper and removing said sulfide compound in a gas phase from said aqueous effluent.

14. The method as recited in claim 13, wherein said stream containing said at least one metal is passed through a metal contactor receiving said sulfide compound in said gas phase and making a contactor outlet stream.

15. The method as recited in claim 14, further comprising the step of passing said contactor outlet stream to a precipitate separator and recycling a metal-free stream to said bioreactor.

16. The method as recited in claim 2, wherein the bacteria are selected from the group consisting of Desulfovibrio, Desulfotomaculum, Desulfococcus, Desulfomonas, Desulfonema, Desulfurococcus, and combinations thereof.

* * * * *